(12) United States Patent
Hong

(10) Patent No.: US 10,537,248 B2
(45) Date of Patent: Jan. 21, 2020

(54) DERMATOSCOPE DEVICE

(71) Applicant: ILLUCO CO., LTD, Gunpo-si, Gyeonggi-do (KR)

(72) Inventor: Jin Hyeok Hong, Bucheon-si (KR)

(73) Assignee: ILLUCO CO., LTD., Gunpo-si (KR)

( * ) Notice: Subject to any disclaimer, the term of this patent is extended or adjusted under 35 U.S.C. 154(b) by 0 days.

(21) Appl. No.: 16/027,042

(22) Filed: Jul. 3, 2018

(65) Prior Publication Data

US 2018/0368692 A1    Dec. 27, 2018

Related U.S. Application Data

(63) Continuation of application No. PCT/KR2017/007309, filed on Jul. 7, 2017.

(30) Foreign Application Priority Data

Jul. 8, 2016  (KR) .................... 10-2016-0087027

(51) Int. Cl.
*A61B 5/00* (2006.01)
*G02B 27/00* (2006.01)
(Continued)

(52) U.S. Cl.
CPC .......... *A61B 5/0077* (2013.01); *A61B 5/0075* (2013.01); *A61B 5/444* (2013.01); *A61B 5/445* (2013.01); *G02B 25/005* (2013.01); *G02B 25/008* (2013.01); *G02B 25/02* (2013.01); *G02B 27/0025* (2013.01); *A61B 5/0064* (2013.01); *A61B 2560/0431* (2013.01);
(Continued)

(58) Field of Classification Search
CPC ..... A61B 5/0077; A61B 5/0075; A61B 5/444; A61B 5/0064; A61B 2560/0431; A61B 2562/0233; G02B 21/36; G02B 25/00; G02B 25/005; G02B 25/008; G02B 25/02; G02B 27/0025; G02B 27/005; G02B 27/286
USPC ........................................................ 362/572
See application file for complete search history.

(56) References Cited

U.S. PATENT DOCUMENTS 7,027,153 B2 †  4/2006  Mullani
2006/0132774 A1  6/2006  Mullani
(Continued)

FOREIGN PATENT DOCUMENTS

KR    10-2009-0033595 A    4/2009

OTHER PUBLICATIONS

International Search Report issued in PCT/KR2017/007309; dated Sep. 25, 2017.
(Continued)

*Primary Examiner* — Anh T Mai
*Assistant Examiner* — Hana S Featherly
(74) *Attorney, Agent, or Firm* — Studebaker & Brackett PC

(57) ABSTRACT

A dermatoscope device is provided. The dermatoscope device includes an optical tube structure including an optical unit, which is provided to allow an observer to enlarge and inspect an observation target, and a light emitting unit which irradiates light to the observation target to be enlarged and inspected through the optical unit, a control module to control a form of irradiating the light through the optical unit, and a housing having the optical tube structure and the control module embedded therein.

10 Claims, 14 Drawing Sheets

(51) Int. Cl.
    *G02B 25/00*     (2006.01)
    *G02B 25/02*     (2006.01)
    *G02B 27/28*     (2006.01)

(52) U.S. Cl.
    CPC .... *A61B 2562/0233* (2013.01); *G02B 27/005* (2013.01); *G02B 27/286* (2013.01)

(56) References Cited

U.S. PATENT DOCUMENTS

2014/0243685 A1*   8/2014   Patwardhan ............ A61B 5/44
                                                                    600/476
2015/0036311 A1    2/2015   Mullani

OTHER PUBLICATIONS

Wang, Hening et al., "Systematic Design of a Cross-Polarized Dermoscope for Visual Inspection and Digital Imaging," IEEE Instrumentation & Measurement Magazine, Dec. 2011, pp. 26-31, Dec. 2011 (6 pages).†

\* cited by examiner
† cited by third party

DERMATOSCOPE DEVICE

CROSS-REFERENCE TO RELATED APPLICATIONS

The present application is a continuation of International Patent Application No. PCT/KR2017/007309, filed Jul. 7, 2017, which is based upon and claims the benefit of priority to Korean Patent Application No. 10-2016-0087027, filed on Jul. 8, 2016. The disclosures of the above-listed applications are hereby incorporated by reference herein in their entirety.

BACKGROUND

Embodiments of the inventive concept described herein relate to dermatoscope devices.

The dermatoscope device is a diagnosis tool used to determine a lesion, such as malignant melanoma, by observing pigmented lesions of skin epidermis and papillary dermis that may not be observed with the naked eyes of an observer. Furthermore, the dermatoscope device is used to diagnose epidermal tumor, papulosquamous disease, and chamois lesion, and to determine a parasite on a skin, in addition to the determination and diagnosis of the pigmented skin lesions.

In other words, the dermatoscope device may provide a larger amount of information than an amount of information which is acquired with a naked eye by an observer, such as, a doctor, and is based on the diagnosis before a biopsy is taken. The dermatoscope device enables the observer to exactly make a diagnosis of a skin lesion and, furthermore, rapidly treat the skin lesion.

Such a dermatoscope device has required the development of a technology allowing an observer making a diagnosis to exactly acquire a larger amount of information by enhancing resolution, reducing a distortion degree, and improving visibility such that the observer more clearly observes an image to be enlarged and observed when observing a skin surface.

In addition, dermatoscope devices having various structures have been developed by taking into consideration the portability and the convenience of a user. To this regard, there has disclosed US2014-0243685 entitled "DERMATOSCOPE DEVICES" (prior art) which is more conveniently used by an observer and liked to another device.

However, the conventional dermatoscope device as well as the prior art have not been sufficiently improved in optical visibility of an enlarged image of an observation target to be observed by the observer. Furthermore, regarding the irradiation of light to the observation target such that lesion on a skin is more clearly observed, the conventional dermatoscope device merely irradiate light or not, or merely polarize light or not.

In other words, according to the conventional dermatoscope device including the prior art, the observer such as the doctor may not delicately adjust the irradiation form of light optimized to the skin condition of a patient, based on the skin condition of the patient.

SUMMARY

Embodiments of the inventive concept provide a dermatoscope device capable of improving visibility to allow a user to more clearly observe an enlarged and observed image by enhancing optical resolution and reducing a distortion degree.

Embodiments of the inventive concept provide a dermatoscope device which can be precisely adjusted and used by a user such that optimized light is irradiated corresponding to a skin condition of a patient.

According to an aspect of an embodiment, a dermatoscope device includes: an optical tube structure including an optical unit, which is provided to allow an observer to enlarge and inspect an observation target, and a light emitting unit which irradiates light to the observation target to be enlarged and inspected through the optical unit; a control module configured to control a form of irradiating the light through the optical unit; and a housing having the optical tube structure and the control module embedded therein. The light emitting unit includes: a light emitting base including a plurality of first light emitting device (LEDs) simultaneously emitting light in response to a first light emitting signal received from the control module and a plurality of second LED parts simultaneously emitting light in response to a second light emitting signal received from the control module; and a first polarizing plate including a plurality of first polarizing parts, which are positioned at a front portion in a direction that the light of the first LED parts is irradiated and have polarizing axes set to a first direction, and a plurality of second polarizing parts which are positioned at a front portion in a direction that the light of the second LED parts is irradiated and have polarizing axes set to a second direction perpendicular to the first direction.

In this case, the first LED parts and the second LED parts may be provided while alternately arranged at equal spacing in a circumferential direction along a specific virtual circumferential line on the light emitting base. The first polarizing parts and the second polarizing parts may be provided corresponding to an alternate arrangement form of the first LED parts and the second LED parts provided on the light emitting base.

The dermatoscope device may further include a polarization controlling input module to a first polarizing signal or a second polarizing signal and to transmit the first polarizing signal or the second polarizing signal to the control module. The control module may generate the first light emitting signal allowing the first LED parts to emit the light, when a signal received through the polarization controlling input module is the first polarizing signal. The control module may generate the second light emitting signal allowing the second LED parts to emit the light, when the signal received through the polarization controlling input module is the second polarizing signal.

In addition, the dermatoscope device may further include a brightness controlling input module to generate brightness control signals classified in at least three stages and to transmit the brightness control signals to the control module. The control module may control brightness of the first LED parts or the second LED parts depending on a brightness stage indicated by a brightness control signal received through the brightness controlling input module.

In addition, the optical unit includes: a first optical lens positioned at a side of the observer and provided in a form of a sectional-surface convex lens which has a convex surface at a side of an observation target; a chromatic aberration lens array positioned in front of the first optical lens at the side of the observation target and having convex opposite surfaces; and a second polarizing plate positioned in front of the chromatic aberration lens array at the side of the observation target and having a polarizing axis set in parallel to the first direction. A radius of curvature of a convex surface of the first optical lens at the side of the observation target is greater than a radius of curvature of a convex surface of the chromatic aberration lens array at a side of the observer and is less than a radius of curvature of a convex surface of the chromatic aberration lens array at the side of the observation target.

In this case, the chromatic aberration lens array includes: a second optical lens positioned in front of the first optical lens at the side of the observation target and having a form of a double-sided convex lens having opposite sides which are convex; and a third optical lens having a form of a negative meniscus lens having a surface which is positioned at the side of the observation target and is concave corresponding to a convex shape of the surface of the second optical lens at the side of the observer while making contact with the surface of the second optical lens at the side of the observer, and a surface which is positioned at the side of the observer is convex. The radius of curvature of the convex surface, which corresponds to the convex surface of the chromatic aberration lens array at the side of the observer, of the second optical lens at the side of the observer is greater than a radius of curvature of the convex surface of the second optical lens at the side of the observation target and is less than the radius of curvature of the convex surface, which corresponds to the convex surface of the chromatic aberration lens array at the side of the observation target, of the third optical lens at the side of the observation target.

The optical unit further includes: a first spacer spacing the first optical lens apart from the chromatic aberration lens array by a first distance; and a second spacer spacing the chromatic aberration lens array apart from the second polarizing plate by a second distance. The first distance, which is formed as central axes of the first optical lens and the chromatic aberration lens array are spaced apart from each other by the first spacer, is shorter than the second distance which is formed as the central axes of the chromatic aberration lens array and the second polarizing plate are spaced apart from each other by the second spacer.

In addition, the optical tube structure includes: a first body part having the optical unit mounted therein, having a first open space, which is open to ensure the field of view for observation, and fixedly coupled to the housing; a second body part having the light emitting unit mounted therein, having a second open space, which is open to ensure the field of view for observation together with the mounted light emitting unit and communicates with the first open space, and fixedly coupled to the first body part or the housing; and a third body part having a third open space, which is open to ensure the field of the view for observation and communicates with the second open space, and a first protective lens provided in an opening of the third open space at the side of the observation target, and coupled to the housing movably back from and forth toward the observation target.

The dermatoscope device may further include: a focal length adjustor coupled to the housing to be linked to the third body part to move the third body part back from and forth toward the observation target such that an enlargement degree of the observation target, which is to be inspected by the observer through the optical unit, is adjusted in zoom in or zoom out.

The dermatoscope device may further include a battery mounted inside the housing to store and supply power required to operate the light emitting unit and the control module; and a charging port configured to supply power to the battery from an outside.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Hereinafter, an exemplary embodiment of the inventive concept will be described in more detail with reference to accompanying drawings and the details of well-known technologies will be omitted or contracted for the clarity of explanation.

Description of Components and Coupling Structure of Dermatoscope Device

In the following description made with reference to FIGS. 1 to 6, according to the inventive concept, a dermatoscope device 1000 includes an optical tube structure 1100, a control module 1200, a housing 1300, a polarization controlling input module 1400, a brightness controlling input module 1500, a focal length adjustor 1600, a battery 1700, and a charging port 1800.

Figure 1:
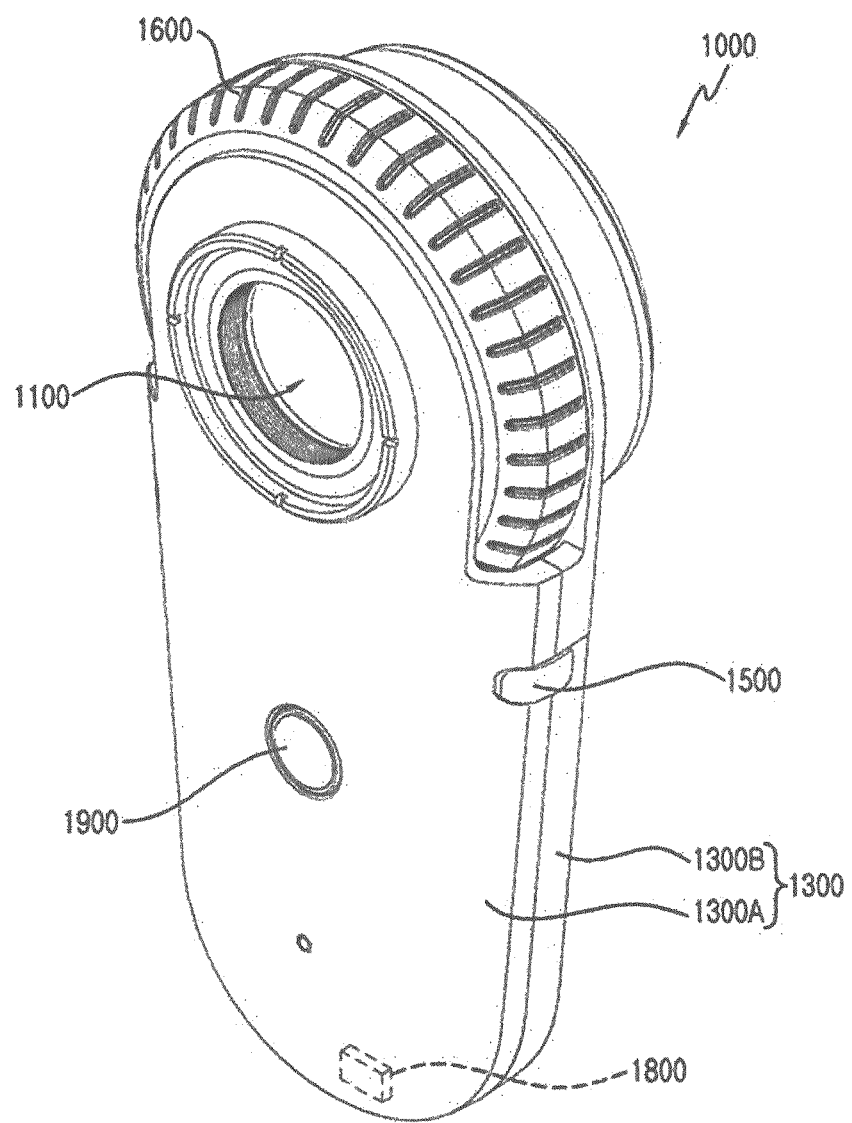
FIGS. 1 and 2 are perspective views illustrating a dermatoscope device, according to the inventive concept.
Figure 1:
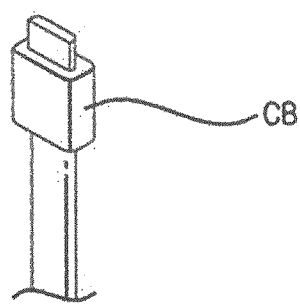
Figure 2:
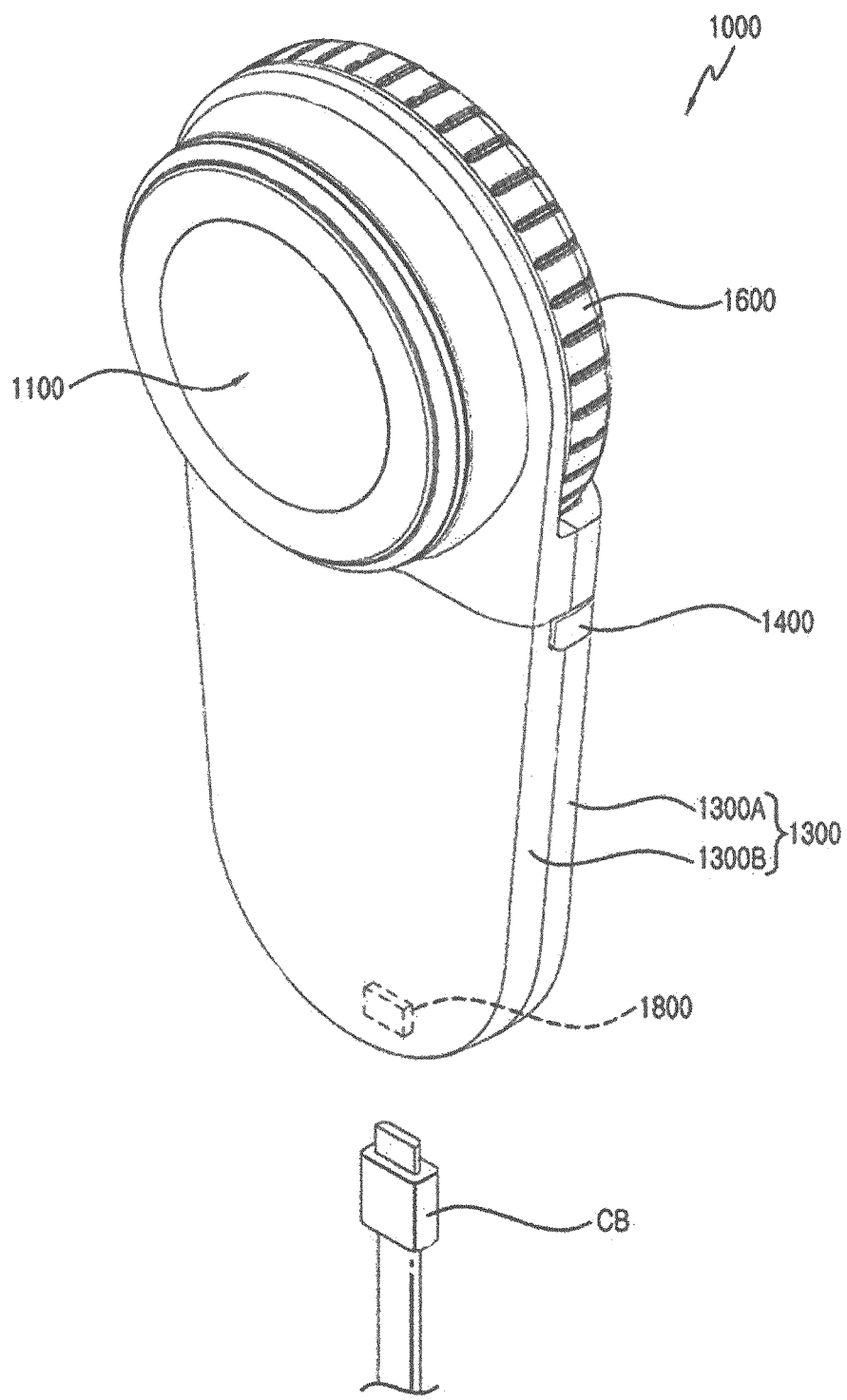
Figure 3:
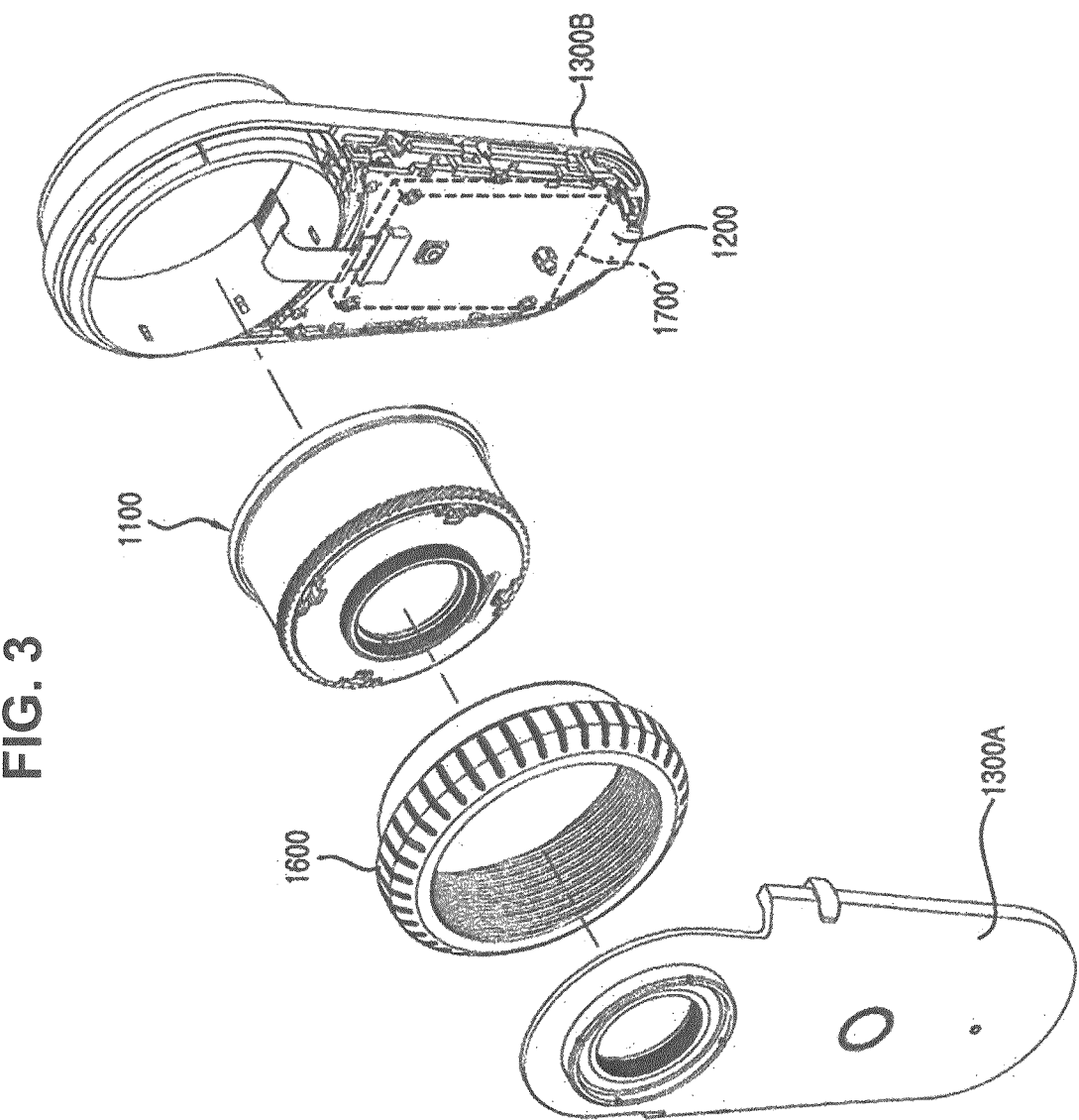
FIG. 3 is an exploded perspective view illustrating components of the dermatoscope device, according to the inventive concept.

The housing 1300 is a body having, therein, various additional components in addition to the optical tube structure 1100, the control module 1200, the polarization controlling input module 1400, the brightness controlling input module 1500, the focal length adjustor 1600, the battery 1700, and the charging port 1800 which constitute the dermatoscope device 1000. As illustrated in FIGS. 1 to 3, the housing 1300 is provided by assembling a first housing part 1300A positioned at the side of an observer and a second housing part 1300B positioned at the side of an observation target.

In this case, the outer appearance of the housing 1300 is provided in the form of a handle such that the observer holds and uses the dermatoscope device 1000 with the hand of the observer as illustrated in FIGS. 1 and 2, and the control module 1200 and the battery 1700 are embedded in the housing 1300. The housing 1300 includes a lower part coupled to the polarization controlling input module 1400 and the brightness controlling input module 1500, which are provided at opposite sides thereof, the charging port 1800, and a power controlling input module 1900 and an upper part coupled to the optical tube structure 1100 and the focal length adjustor 1600, which are to be described below, to allow the observer to observe the skin tissue.

Figure 4:
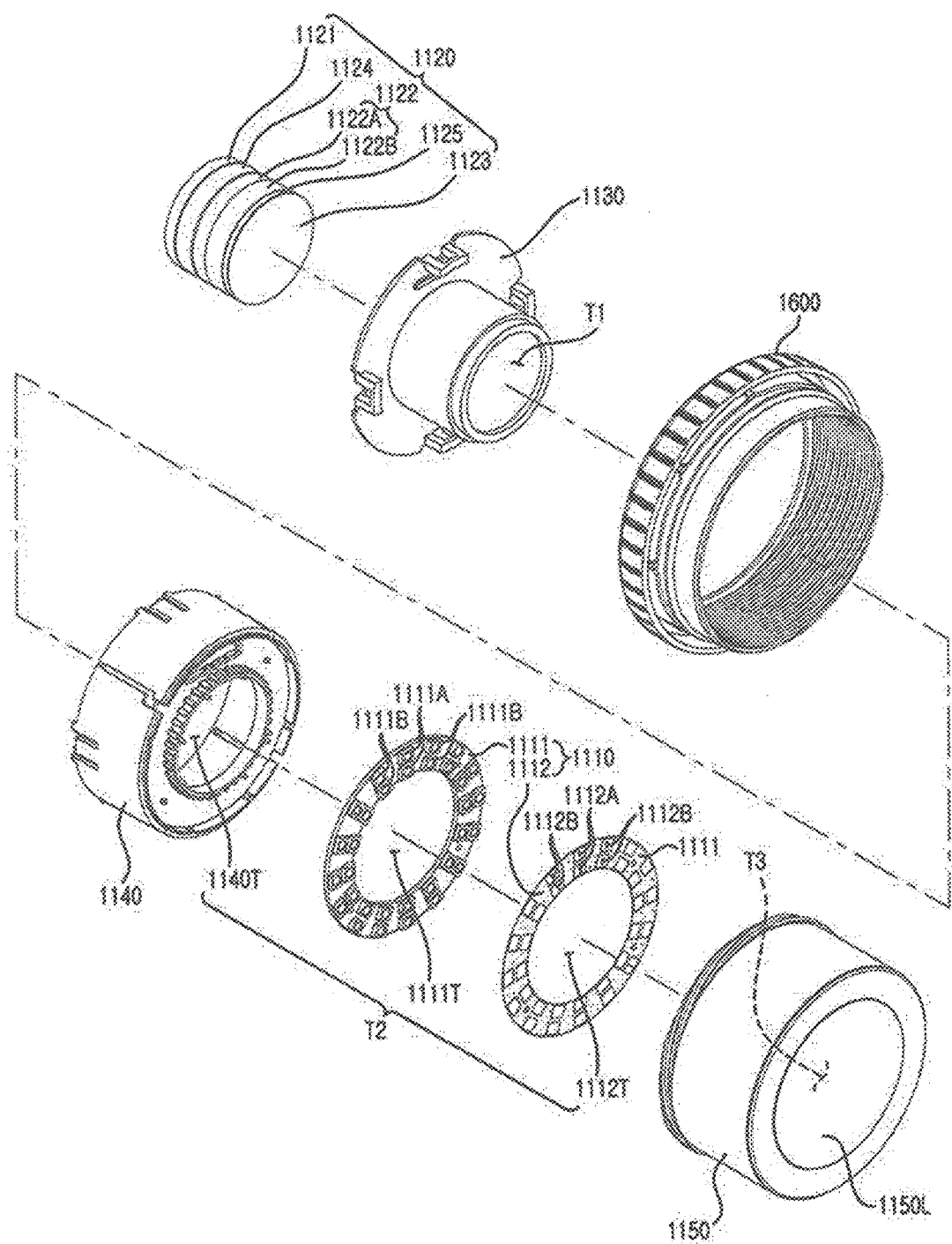
FIG. 4 is an exploded perspective view illustrating detailed components of an optical tube structure of the dermatoscope device, according to the inventive concept.

The optical tube structure 1100 is, as illustrated in FIG. 4, a component to substantially provide optical characteristics and functions of the dermatoscope device 1000 of the inventive concept through an optical unit 1120, which is provided to allow the observer to enlarge and inspect an observation target, and a light emitting unit 1110 which irradiates light to the periphery of the observation target to be enlarged and inspected through the optical unit 1120.

The light irradiation form of light irradiated through the light emitting unit 1110 of the optical tube structure 1100, in more detail, the polarization providing form and the brightness degree of the light are controlled through the control module 1200.

In addition, electrical energy necessary for operating the light emitting unit 1110 and the control module 1200 is supplied from power charged in the battery 1700. To charge the battery 1700 the electrical energy in the battery 1700, the dermatoscope device 1000 of the inventive concept additionally includes the charging port 1800.

The charging port 1800 is preferably provided to be electrically connected with a universal serial bus (USB)-type connection terminal having a 5-pin structure of a charging cable CB connected with a power supply so as to easily receive power from various external devices, but is not limited thereto. For example, the charging port 1800 may be variously designed to be modified corresponding to the shapes of connection terminals of various charging cables CB such that the charging port is connected with the connection terminals.

In this case, the light emitting unit 1110 includes a light emitting base 1111, which includes light emitting members 1111A and 1111B, such as a plurality of light emitting devices (LEDs), and has the shape of a disk including a hollow 1111T in a donut shape, and a first polarizing plate 1112 which includes two types of polarizing films 1112A and 1112B having mutually different polarizing axes and dividing the first polarizing plate 1112 into multiple areas and has the shape of a disk including a hollow 1112T in a donut shape.

The disk-type light emitting base 1111 includes a plurality of first LED parts 1111A simultaneously emitting light in response to a first light emitting signal received from the control module 1200 and a plurality of second LED parts 1111B simultaneously emitting light in response to a second light emitting signal received from the control module 1200.

Figure 6:
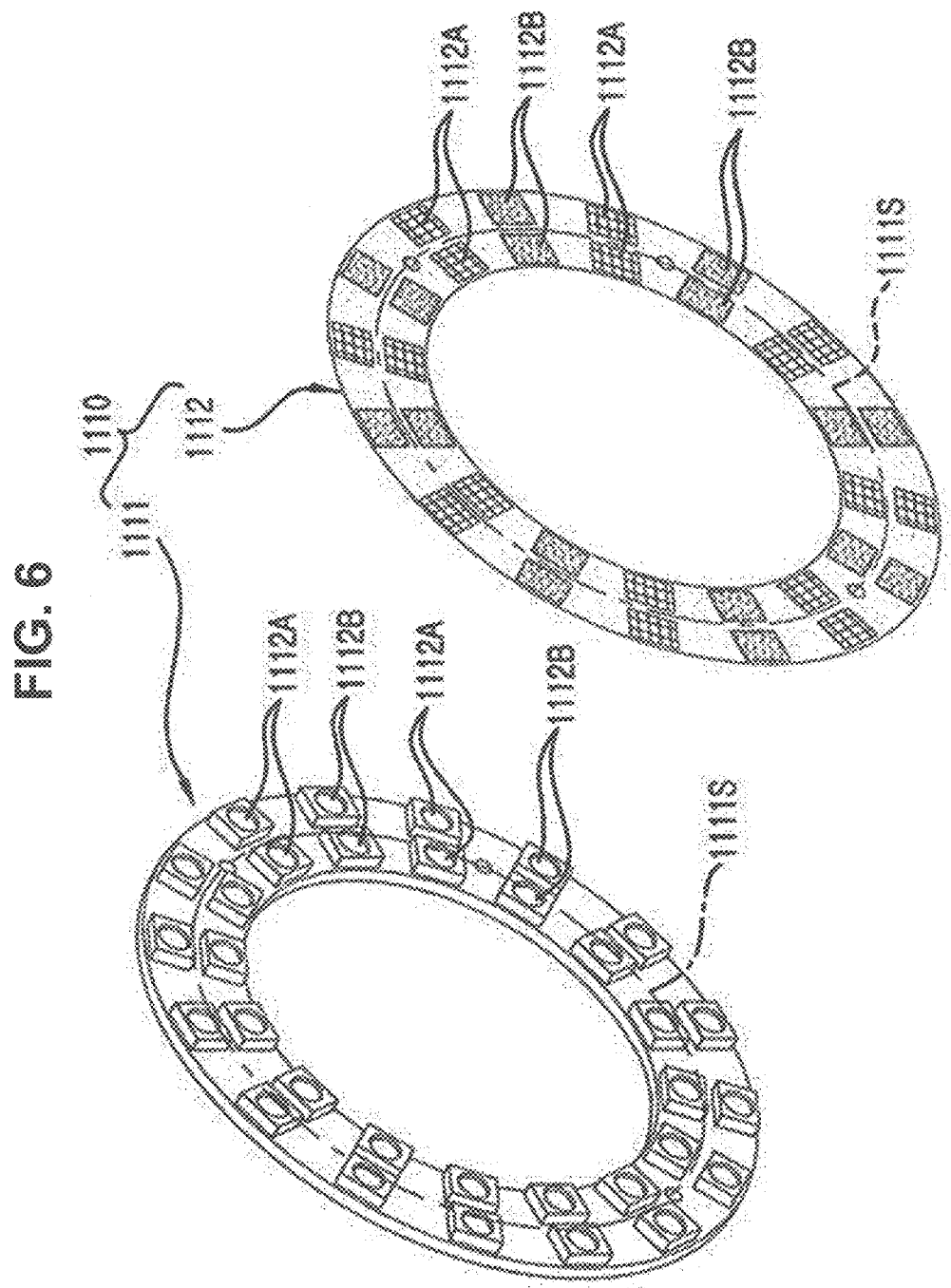
FIG. 6 is an exploded perspective view illustrating detailed components of a light emitting unit in the optical tube structure, according to the inventive concept.
Figure 7:
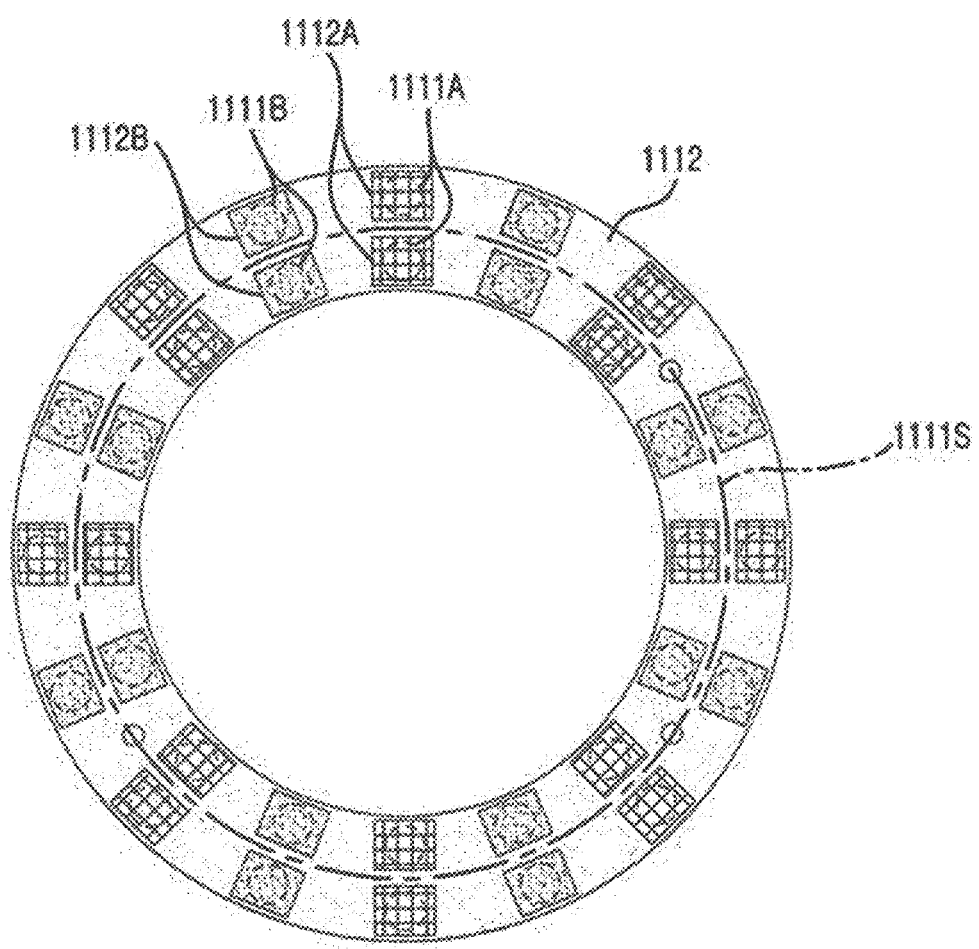
FIG. 7 is a front view illustrating the coupling structure between detailed components of the light emitting unit in the optical tube structure, according to the inventive concept.

The first LED parts 1111A and the second LED parts 1111B are installed on the light emitting base 1111 while alternately arranged at equal spacing along a virtual circumferential line 1111S (in a circumferential direction) which may be arbitrarily set on the light emitting base 1111 having the shape of the disk including the hollow 1111T as illustrated in FIGS. 6 and 7.

Accordingly, the irradiation range of light is rarely changed between the case of emitting light from the first LED parts 1111A on the light emitting base 1111 as the first light emitting signal is received from the control module 1200 and the case of emitting light from the second LED parts 1111B on the light emitting base 1111 as the second light emitting signal is received from the control module 1200. In other words, even if a polarizing function is changed, the observer may receive light to a certain periphery of the observation target without deviation.

In addition, the first LED parts 1111A and the second LED parts 1111B, which are alternately arranged at equal spacing along the virtual circumferential line 1111S (in the circumferential direction), may uniformly irradiate light to the observation target depending on preset brightness of light.

The first polarizing plate 1112, which has the shape of the disk including the hollow 1112T in the donut shape, is arranged in front of the light emitting base 1111 in a direction that light is irradiated through the first LED parts 1111A and the second LED parts 1111B.

The first polarizing plate 1112 is provided such that a plurality of first polarizing parts 1112A having polarizing axes set to a first direction are positioned in front of the first LED parts 1111A in the direction that light is irradiated from the first LED parts 1111A as illustrated in FIG. 7 and a plurality of second polarizing parts 1112B having polarizing axes set to a second direction perpendicular to the first direction as illustrated in FIG. 6 are positioned in front of the second LED parts 1111B in the direction (toward the observation target) that light is irradiated from the second LED parts 1111B.

Figure 5:
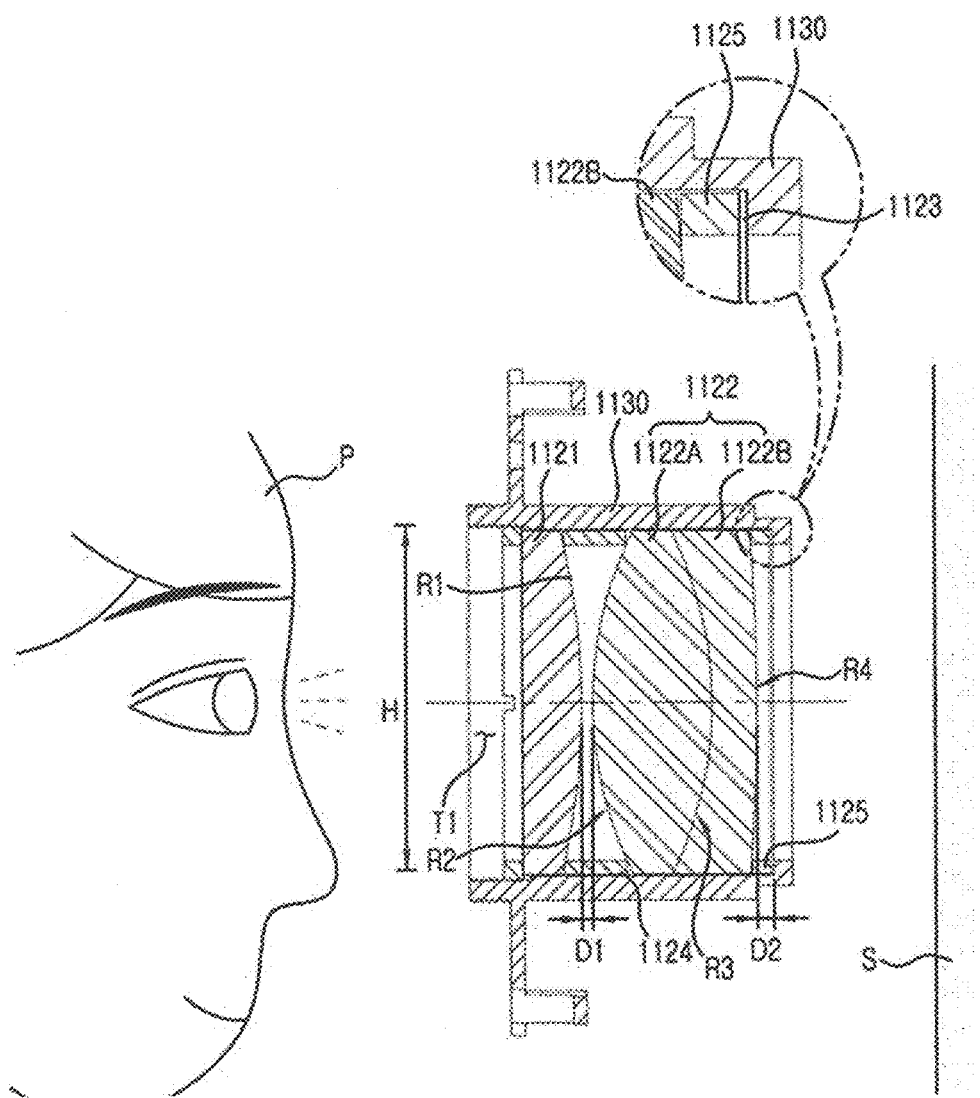
FIG. 5 is a sectional view illustrating the coupling structure between detailed components of an optical unit in the optical tube structure, according to the inventive concept.

In other words, as illustrated in FIGS. 5 and 6, the first polarizing parts 1112A and the second polarizing parts 1112B are alternately arranged on the first polarizing plate 1112 having the shape of the disk including the hollow 1112T in the donut shape to correspond to the first LED parts 1111A and the second LED parts 1111B alternately arranged at equal spacing along the virtual circumferential line 1111S (in the circumferential direction) arbitrarily set on the light emitting base 1111 having the shape of the disk including the hollow 1111T.

When light is irradiated as the first light emitting signal is received from the control module 1200 and thus the first LED parts 1111A on the light emitting base 1111 emit light, the light is polarized in the polarizing axes set to the first direction through the first polarizing parts 1112A. In addition, when light is irradiated as the second light emitting signal is received from the control module 1200 and thus the second LED parts 1111B on the light emitting base 1111 emit light, the light is polarized in the polarizing axes, which are set to the second direction perpendicular to the first direction, through the second polarizing parts 1112B. Accordingly, mutually different polarizations of light forms may be provided.

To selectively provide parallel polarization or cross polarization as described above, the dermatoscope device 1000 of the inventive concept further includes the polarization controlling input module 1400.

The polarization controlling input module 1400 includes a switch for inducing the generation of a command signal as being pressed or touched by the user (observer). According to an embodiment, the polarization controlling input module 1400 may be provided in the form having a configuration to process a specific command signal based on a signal input through the switch and to transmit the processing result to the control module 1200 such that an additional command signal is generated. In addition, the polarization controlling input module 1400 may be provided in the form allowing the control module 1200 to generate a specific command signal based on a signal input through the switch when the input signal is received in the control module 1200.

Accordingly, when the user (or the observer) presses or touches the switch included in the polarization controlling input module 1400 to make an input, the polarization controlling input module 1400 generates the first polarizing signal or the second polarizing signal and transmits the first polarizing signal or the second polarizing signal to the control module 1200.

In this case, the first polarizing signal or the second polarizing signal may correspond to the specific command signal processed based on the signal input through the switch, and the control module 1200 receiving the first polarizing signal or the second polarizing signal may generate a light emitting signal corresponding to the command signal. Alternatively, the first polarizing signal or the second polarizing signal may correspond to the signal input through the switch, and the control module 1200 receiving the first polarizing signal or the second polarizing signal may generate the light emitting signal as the specific command signal, based on the first polarizing signal or the second polarizing signal.

In addition, the polarization controlling input module 1400 may be provided to include one switch and to transmit mutually different polarizing signals to the control module 1200 depending on a pressing or touching count. Alternatively, the polarization controlling input module 1400 may be provided to include a plurality of switches and to transmit mutually different polarizing signals to the control module 1200 depending on switches touched or pressed.

Accordingly, when a signal received in the control module 1200 from the polarization controlling input module 1400 is the first polarizing signal, the control module 1200 generates a first light emitting signal allowing the first LED parts 1111A to emit light such that light emission is controlled, thereby irradiating the periphery of the observation target with light polarized in the polarizing axes, which set to the first direction, through the first polarizing parts 1112A.

When a signal received in the control module 1200 from the polarization controlling input module 1400 is the second polarizing signal, the control module 1200 generates the second light emitting signal allowing the second LED parts 1111B to emit light such that light emission is controlled, thereby irradiating the periphery of the observation target with light polarized in the polarizing axes, which set to the second direction, through the second polarizing parts 1112B.

In addition, the dermatoscope device 1000 of the inventive concept further includes the brightness controlling input module 1500 to selectively adjust the brightness of the light, which is irradiated through the first LED parts 1111A or the second LED parts 1111B, in multiple stages.

The brightness controlling input module 1500 is configured to generate brightness control signals classified in multiple stages such as at least three stages and to transmit the bright control signals to the control module 1200. The brightness controlling input module 1500 includes a switch for inducing the generation of a command signal as being pressed or touched by the user (observer). According to an embodiment, the brightness controlling input module 1500 may be provided in the form having a configuration to process a specific command signal based on a signal input through the switch and to transmit the processing result to the control module 1200 such that an additional command signal is generated. In addition, the brightness controlling input module 1500 may be provided in the form allowing the control module 1200 to generate a specific command signal based on a signal input through the switch when the input signal is received in the control module 1200.

Accordingly, when the user (or the observer) presses or touches the switch included in the brightness controlling input module 1500 to make an input, the brightness controlling input module 1500 generates brightness control signals classified in multiple stages and transmits the bright control signals to the control module 1200.

For example, when the user (or the observer) presses or touches the switch included in the brightness controlling input module 1500 one time, the brightness controlling input module 1500 generates a brightness control signal (first-stage brightness control signal) provided in a first stage and transmits the first-stage brightness control signal to the control module 1200. When the user (or the observer) presses or touches the switch included in the brightness controlling input module 1500 twice, the brightness controlling input module 1500 generates a brightness control signal (second-stage brightness control signal), which is provided in a second stage, for controlling the brightness higher than that of the first-stage brightness control signal and transmits the second-stage brightness control signal to the control module 1200.

In addition, it is preferred that an upper limit stage is preset in controlling the brightness in multiple stages. For example, when the upper limit stage is a fifth stage, the switch included in the brightness controlling input module 1500 is configured such that the case of six presses or touches by a user (observer) is processed identically to the case of one press or touch by the user.

In this case, the brightness control signals classified in the multiple stages may correspond to the specific command signal processed based on the signals input through the switch, and the control module 1200 receiving the brightness control signals may generate a light emitting signal corresponding to the command signal. Alternatively, the brightness control signals may correspond to signals input through the switch, and the control module 1200 receiving the brightness control signals may generate light emitting signals as specific command signals based on the brightness control signals.

Accordingly, the control module 1200 may control the brightness of the first LED parts 1111A and the second LED parts 1111B depending on brightness stages indicated by the brightness control signals received through the brightness controlling input module 1500.

Therefore, the user (observer) may precisely adjust the brightness of polarized light irradiated to the periphery of the observation target to receive an image showing the optimal optical characteristic in association with the states (the color of the skin, the color of lesion, the size of the lesion, the irregularity degree of a skin surface, the degree of foreign substances on the skin surface, or the use of emulsion oil) of the skin of the user, which serves as the observation target.

Regarding the control for the form of irradiating light by using the polarization controlling input module 1400 and the brightness controlling input module 1500 as described above, the irradiation state of light (which serves as a first premise) is determined depending on whether power is supplied to the input modules 1400 and 1500, the control module 1200, and the light emitting unit 1110 from the battery 1700 through the power controlling input module 1900.

The power controlling input module 1900 includes a switch for inducing the generation of a command signal as being pressed or touched by the user (observer). According to an embodiment, the power controlling input module 1900 may be provided in the form having a configuration to process a specific command signal based on a signal input through the switch and to transmit the processing result to the control module 1200 such that an additional command signal is generated. In addition, the power controlling input module 1900 may be provided in the form allowing the control module 1200 to generate a specific command signal based on a signal input through the switch when the input signal is received in the control module 1200.

Accordingly, when the user (or the observer) presses or touches the switch included in the power controlling input module 1900 to make an input, the power controlling input module 1900 allows the battery 1700 to supply power such that the functions of the polarization controlling input module 1400, the brightness controlling input module 1500, the control module 1200, and the light emitting unit 1110 are activated.

Furthermore, the control module 1200 further include an additional memory unit (not illustrated) storing information representing which LED emits light based on a signal received from the polarization controlling input module 1400 and the number of brightness stages set for the first LED parts 1111A or the second LED parts 1111B through the brightness controlling input module 1500, in the last function activation state (power-on state) before the power controlling input module 1900 allows the battery 1700 to supply power based on a pressing or touching count to activate the function of various components.

Accordingly, when the power controlling input module 1900 allows the battery 1700 to supply power by the pressing or touching count to activate the functions of various components, the control module 1200 detects the last control form for light irradiation stored in the memory unit and initially outputs the light, in which the control form is reflected without change.

The control form of light irradiation based on the pressing or touching count right before the power controlling input module 1900 shuts off the supplying of power from the battery 1700 is reflected, without change, in the case that the power controlling input module 1900 allows the battery 1700 to supply power based on the pressing or touching count.

The optical unit 1120 is a component to provide an optical characteristic when an observer P observes an observation target S in an enlarged image. The optical unit 1120 includes a plurality of optical lenses and polarizing plates, and the optical characteristic is more enhanced due to the settings of the gaps between the optical lenses and polarizing plates and the differentiated settings of the radiuses of curvature.

To this end, as illustrated in FIG. 5, the optical unit 1120 may include a first optical lens 1121, a chromatic aberration lens array 1122, a second polarizing plate 1123, a first spacer 1124, and a second spacer 1125.

In this case, as illustrated in FIG. 5 the first optical lens 1121 is positioned at the side of the observer P when viewed from the whole structure of the optical unit 1120 and provided in the form of a sectional-surface convex lens having a convex surface at the side of the observation target S.

In addition, the chromatic aberration lens array 1122 corresponds to an adhesive achromatic lens positioned in front of the first optical lens 1121 at the side of the observation target S and including the second optical lens 1122A, which are convex at opposite sides thereof and serves as a lens adherend, and the third optical lens 1122B.

In this case, the second optical lens 1122A has the form of a double-sided convex lens convex at the opposite sides thereof. The second optical lens 1122A is positioned in front of the first optical lens 1121 at the side of the observation target S. The convex surface of the second optical lens 1122A at the side of the observer P corresponds to a convex surface of the chromatic aberration lens array 1122 at the side of the observer P.

In addition, the third optical lens 1122B has the form of a negative meniscus lens having a convex surface at the side of the observation target S. As illustrated in FIG. 5, the surface of the third optical lens 1122B at the side of the observer P has a concave shape corresponding to a convex shape of the surface of the second optical lens 1122A at the side of the observation target S to make contact with the surface of the second optical lens 1122A at the side of the observation target S. As illustrated in FIG. 5, the convex surface of the third optical lens 1122B at the side of the observation target S corresponds to a convex surface of the chromatic aberration lens array 1122 at the side of the observation target S.

In addition, as illustrated in FIG. 5, the second polarizing plate 1123 is positioned in front of the chromatic aberration lens array 1122 at the side of the at the side of the observation target S and has a polarizing axis set in parallel to the first direction the same as the polarizing axis of the first polarizing parts 1112A of the first polarizing plate 1112.

Accordingly, the light irradiated through the first LED parts 1111A is provided, in the state of being primarily polarized through the first polarizing parts 1112A, to a certain area around the observation target S, and the light which is reflected from the observation target S and is incident on the second polarizing plate 1123, provides a parallel polarizing function to the observer P.

In addition, the light irradiated through the second LED parts 1111B is provided, in the state of being primarily polarized through the second polarizing parts 1112B, to a certain area around the observation target S, and the light, which is reflected from the observation target S and is incident on the second polarizing plate 1123, provides a cross polarizing function to the observer P.

The first spacer 1124 spaces the first optical lens 1121 apart from the chromatic aberration lens array 1122 by a first distance D1, and the second spacer 1125 spaces the chromatic aberration lens array 1122 apart from the second polarizing plate 1123 by a second distance D2.

The relative relation in the radius of curvature between the first optical lens 1121 and the second optical lens 1122A and the third optical lens 1122B constituting the chromatic aberration lens array 1122, the spacing between the first optical lens 1121 and the chromatic aberration lens array 1122 by the first spacer 1124, the spacing between the chromatic aberration lens array 1122 and the second polarizing plate 1123 by the second spacer 1125 more enhance optical resolution and more reduce an image distortion.

In detail, the radius R1 of curvature of the convex surface of the first optical lens 1121 at the side of the observation target S is preferably provided to be greater than the radius R2 of curvature of the convex surface of the second optical lens 1122A at the side of the observer P, which corresponds to the convex surface of the chromatic aberration lens array 1122 at the side of the observer P, and to be less than the radius R4 of curvature of the convex surface of the third optical lens 1122B at the side of the observation target S which corresponds to the convex surface of the chromatic aberration lens array 1122 at the side of the observation target S.

In addition, the radius R2 of curvature of the convex surface of the second optical lens 1122A at the side of the observer P is preferably provided to be greater than the radius R3 of curvature of the convex surface of the second optical lens 1122A at the side of the observation target S and to be less than the radius R4 of curvature of the convex surface of the third optical lens 1122B at the side of the observation target S.

Accordingly, the size of the radius of curvature is provided in descending order of the radius R4 of curvature of the convex surface of the third optical lens 1122B at the side of the observation target S, the radius R1 of curvature of the convex surface of the first optical lens 1121 at the side of the observation target S, the radius R2 of curvature of the convex surface of the second optical lens 1122A at the side of the observer P, and the radius R3 of curvature of the convex surface of the second optical lens 1122A at the side of the observation target S.

In addition, preferably, the distance D1 between the central axes of the first optical lens 1121 and the chromatic aberration lens array 1122 spaced apart from each other by the first spacer 1124 is shorter than the distance D2 between the central axes of the chromatic aberration lens array 1122 and the second polarizing plate 1123 spaced apart from each other by the second spacer 1125.

In more detail, based on that the radius R1 of curvature of the convex surface of the first optical lens 1121 at the side of the observation target S is in the range of 51 mm to 52 mm (preferably, is 51.6 mm), the radius R2 of curvature of the convex surface of the second optical lens 1122A at the side of the observer P is in the range of 27.5 mm to 28.5 mm (preferably, 28 mm), the radius R3 of curvature of the convex surface of the second optical lens 1122A at the side of the observation target S is in the range of 18.5 mm to 19.5 mm (preferably, 19 mm), and the radius R4 of curvature of the convex surface of the third optical lens 1122B at the side of the observation target S is in the range of 152.5 mm to 153.5 mm (preferably, 153 mm)

In addition, more preferably, the distance D1 between the central axes of the first optical lens 1121 and the chromatic aberration lens array 1122 spaced apart from each other by the first spacer 1124 is in the range of 0.8 mm to 0.82 mm (preferably, 0.81 mm), and the distance D2 between the central axes of the chromatic aberration lens array 1122 and the second polarizing plate 1123 spaced apart from each other by the second spacer 1125 is in the range of 0.9 mm to 1.1 mm (preferably, 1.0 mm).

In more detail, the surface of the first optical lens 1121 at the side of the observation target S and both surfaces of the second optical lens 1122A and the third optical lens 1122B are preferably subject to BroadBand Anti Reflection (BBAR) coating to reduce the transmittance of ultraviolet light and infrared light and the light reflectance and to maximize the transmittance of visible light having the wavelength band in the range of 380 nm to 780 nm.

In addition, the first optical lens 1121 has the refractive index in the range of 1.51 to 1.52 (preferably, 1.517), the second optical lens 1122A has the refractive index in the range of 1.66 to 1.67 (preferably, 1.667), and the third optical lens 1122B has the refractive index in the range of 1.72 to 1.73 (preferably, 1.728).

The features of the first optical lens 1121, the second optical lens 1122A, and the third optical lens 1122B will be summarized in table 1 in terms of lens specifications.

TABLE 1

(RE1: the surface at the side of an observer, RE2: the surface at the side of the observation target)

| | $1^{st}$ optical lens 1121 | $2^{nd}$ optical lens 1122A | $3^{rd}$ optical lens 1122B |
|---|---|---|---|
| Embodiment | N-BK7 of SCHOTT | BAF11 of HOYA | N-SF10 of SCHOTT |
| NR | RE1 = 3 fringes | RE1 = 3 fringes | RE1 = 3 fringes |
| | RE2 = 3 fringes | RE2 = 3 fringes | RE2 = 3 fringes |
| AS | RE1 = 0.5 fringes | RE1 = 0.8 fringes | RE1 = 0.8 fringes |
| | RE2 = 1.0 fringes | RE2 = 0.8 fringes | RE2 = 0.8 fringes |
| Excentric | −1' | −1' | −1' |
| Whole diameter | 25 mm | 25 mm | 25 mm |
| Clear Aperture | RE1 = 24.5 mm | RE1 = 24.5 mm | RE1 = 24.5 mm |
| | RE2 = 24.5 mm | RE2 = 24.5 mm | RE2 = 24.5 mm |
| Center Thickness | 4.35 ± 0.02 | 9.50 ± 0.02 | 2.50 ± 0.02 |
| Edge Thickness | 2.81 | 1.864 | 6.68 |
| Coating | RE1 = LB coating RE2 = BBAR coating @400-700 nm, R < 1% | RE1, RE2 = BBAR coating @400-700 nm, T > 98% | RE1, RE2 = BBAR coating @400-700 nm, T > 98% |
| Refractive index | 1.517 | 1.667 | 1.728 |

The surface of the first optical lens 1121 at the side of the observer P is subject to light balancing (LB) coating instead of BBAR coating, which is different from the surface of the first optical lens 1121 at the side of the observation target S. The surface subject to LB coating serves as a filter to reduce a blue light region and a yellow light region occupying the most part of LED light, which is irradiated from the first LED parts 1111A or the second polarizing parts 1112B of the light emitting base 1111, when observed through the naked eyes of the observer P due to the characteristics of the LED light. Accordingly, the balance of light transmitted through the eyes of the observer P is maintained such that the light becomes closer to natural light.

As a result, coating design results of a coating film having a multi-layer thin film structure, which is provided by coating the surface of the first optical lens 1121 at the side of the observer P, are classified according to a physical thickness and an optical thickness and summarized as illustrated in Table 2.

TABLE 2

| Thin film layer (Layer) | Coating compound | Refractive index (Index) | Optical thickness [FWOT] | Physical thickness [nm] |
|---|---|---|---|---|
| 1 | SiO₂ | 1.45@440 nm | 0.1900 | 79.88 |
| 2 | TiO₂ | 2.35@460 nm | 0.3475 | 97.99 |
| 3 | SiO₂ | 1.45@440 nm | 0.3943 | 165.76 |
| 4 | TiO₂ | 2.35@460 nm | 0.3929 | 110.8 |
| 5 | SiO₂ | 1.45@440 nm | 0.4150 | 174.46 |
| 6 | TiO₂ | 2.35@460 nm | 0.3924 | 110.67 |
| 7 | SiO₂ | 1.45@440 nm | 0.4793 | 201.48 |
| 8 | TiO₂ | 2.35@460 nm | 0.0912 | 25.73 |
| 9 | SiO₂ | 1.45@440 nm | 0.1260 | 52.96 |
| 10 | TiO₂ | 2.35@460 nm | 0.0647 | 18.26 |
| 11 | SiO₂ | 1.45@440 nm | 0.5066 | 212.96 |
| 12 | TiO₂ | 2.35@460 nm | 0.6697 | 188.86 |
| 13 | SiO₂ | 1.45@440 nm | 0.7066 | 297.02 |
| 14 | TiO₂ | 2.35@460 nm | 0.5859 | 165.23 |
| 15 | SiO₂ | 1.45@440 nm | 0.0392 | 16.48 |
| 16 | TiO₂ | 2.35@460 nm | 0.0514 | 14.49 |

The coating design results of the coating film having a multi-layer thin film structure, which is provided by coating the surface of the first optical lens 1121 at the side of the observer P, are obtained by designing light to be closer to natural light after detecting the color temperature characteristic of each wavelength of LED light irradiated from the first LED parts 1111A or the second LED parts 1111B of the light emitting base 1111.

In other words, the first optical lens 1121 maintains the balance of the LED light irradiated from the first LED parts 1111A or the second LED parts 1111B of the light emitting base 1111 through the above-described LB coating before being transmitted to the eyes of the observer P such that the light closer to natural light is provided to the observer P, thereby protecting the eyes of the observer P, lowering the degree of fatigue applied to the eyes even in the long-term observation, and significantly improving the visibility in the observation of a target.

Figure 8:
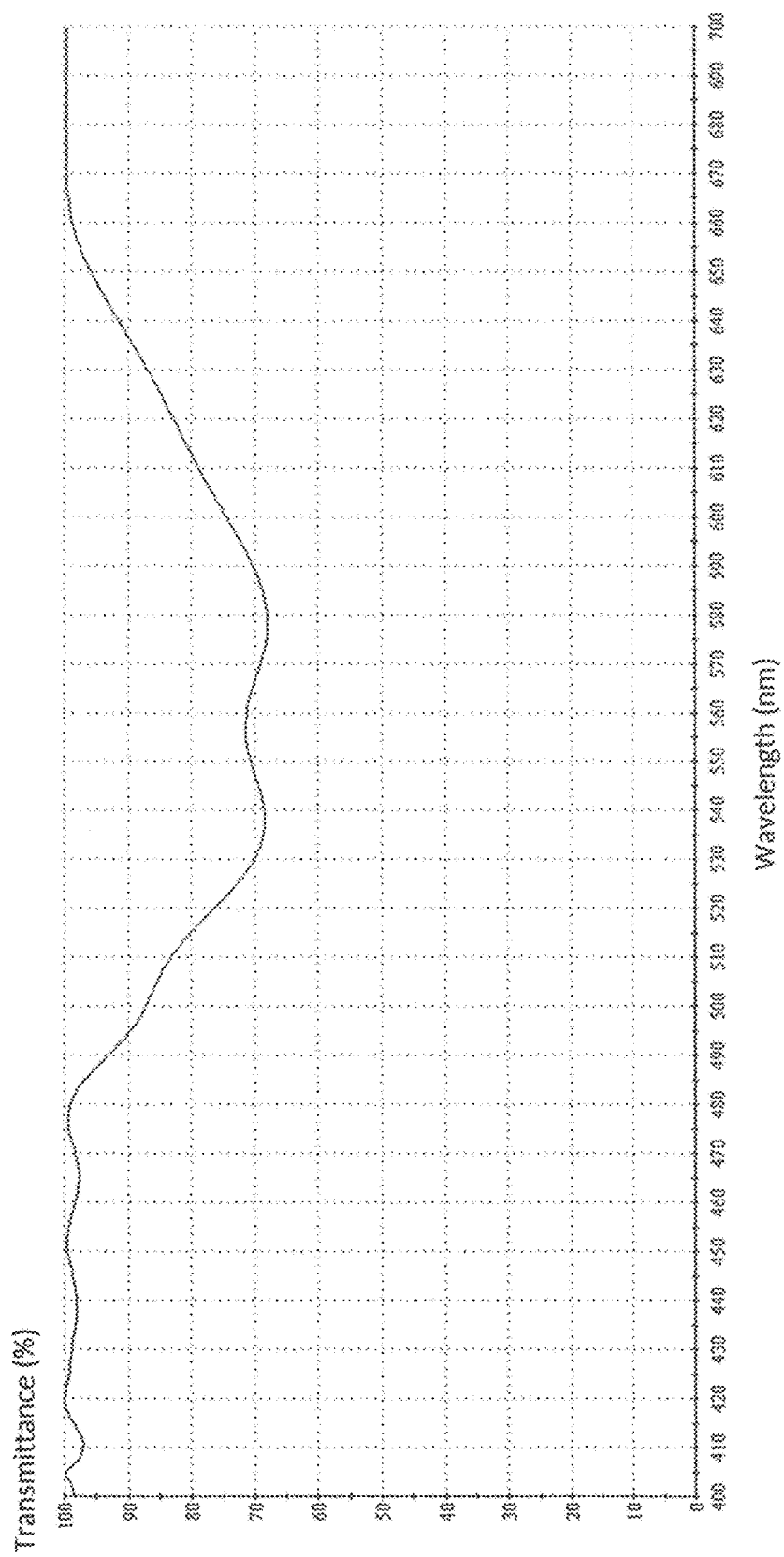
FIG. 8 is a graph illustrating the measurement result of a transmittance spectrum of a first optical lens installed in the dermatoscope device, according to the inventive concept.

To determine the optical characteristic based on the coating design results of the coating film having the multi-layer thin film structure, which is provided by coating the surface of the first optical lens 1121 at the side of the observer P, the light transmittance spectrum of the first optical lens 1121 is measured by using a spectrophotometer and the measurement result is represented as illustrated in FIG. 8.

As illustrated in FIG. 8, it may be recognized that the first optical lens 1121 blocks blue light and yellow light to the higher extent through the LB coating-based multi-layer coating thin film formed on the surface at the side of the observer P and the whole wavelengths are significantly closer to the wavelengths of natural light.

Meanwhile, the first optical lens 1121 is subject to the BBAR coating on the surface at the side of the observation target S to reduce the reflectance of the lens and increase the transmittance of the lens, thereby preventing the glare of the observer and improving the optical definition to solve the problem of interrupting the concentration of the observer and the accuracy in the observation and the judgment of the observer.

Accordingly, the coating design results of the coating film having the multi-layer thin film structure, which is provided by coating the surface of the first optical lens 1121 at the side of the observer P, are classified according to the physical thickness and the optical thickness as illustrated in Table 3.

TABLE 3

| Thin film layer (Layer) | Coating compound | Refractive index (Index) | Optical thickness [FWOT] | Physical thickness [nm] |
|---|---|---|---|---|
| 1 | Al₂O₃ | 1.63@475 nm | 0.2698 | 78.4301 |
| 2 | ZrO₂/TiO | 2.07@475 nm | 0.3792 | 86.9037 |
| 3 | Al₂O₃ | 1.63@475 nm | 0.0143 | 4.1749 |
| 4 | ZrO₂/TiO | 2.07@475 nm | 0.1425 | 32.6572 |
| 5 | MgF₂ | 1.38@480 nm | 0.2701 | 93.8185 |

Figure 9:
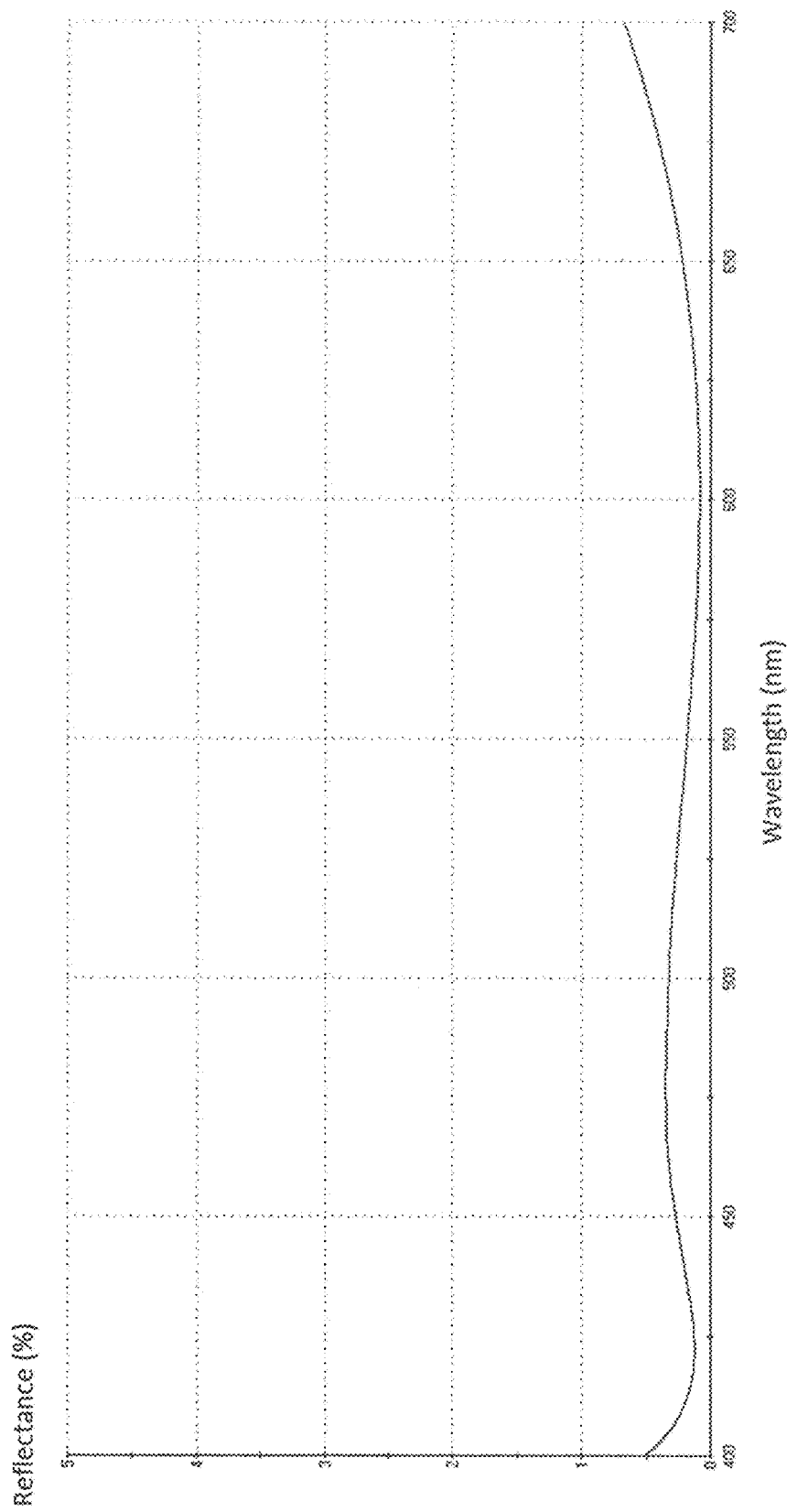
FIG. 9 is a graph illustrating the measurement result of a reflectance spectrum of the first optical lens installed in the dermatoscope device, according to the inventive concept.

To determine the optical characteristic based on the coating design results of the coating film having the multi-layer thin film structure, which is provided by coating the surface of the first optical lens 1121 at the side of the observation target S, the light reflectance spectrum of the first optical lens 1121 is measured by using a spectrophotometer and the measurement result is represented as illustrated in FIG. 9.

As illustrated in FIG. 9, it may be recognized that the first optical lens 1121 represents, in the reflectance and the transmittance of light, levels, which are appropriate to prevent the glare of the observer and to improve the optical definition, through the BBAR coating-based multi-layer coating thin film formed on the surface at the side of the observation target S under the environment that LED light is irradiated to the observation target S from the first LED parts 1111A and the second LED parts 1111B of the light emitting base 1111.

The design of the BBAR coating for the surface positioned at the side of the observation target S and the multi-layer thin film structure based on the design result are identically applied to opposite surfaces of the second optical lens 1122A and the third optical lens 1122B.

The enhancement degree of the optical characteristic provided by the optical unit 1120 of the dermatoscope device 1000 of the inventive concept having the specific physical and optical specifications may be obtained through the optical inspection result as illustrated in FIGS. 10 to 14.

Figure 10:
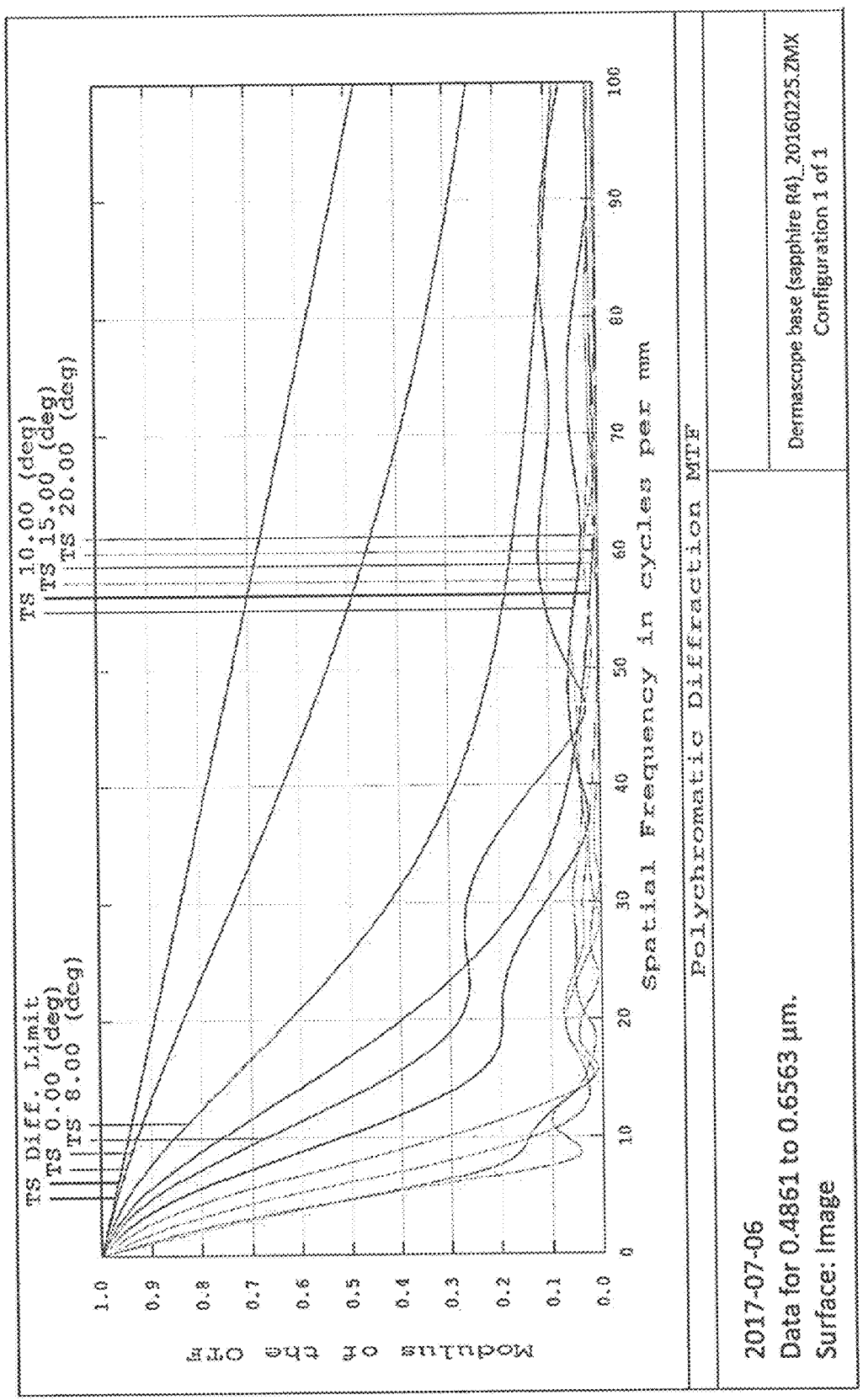
FIG. 10 is a graph illustrating an inspection result of optical resolution using the optical tube structure of the dermatoscope device, according to the inventive concept.
Figure 11:
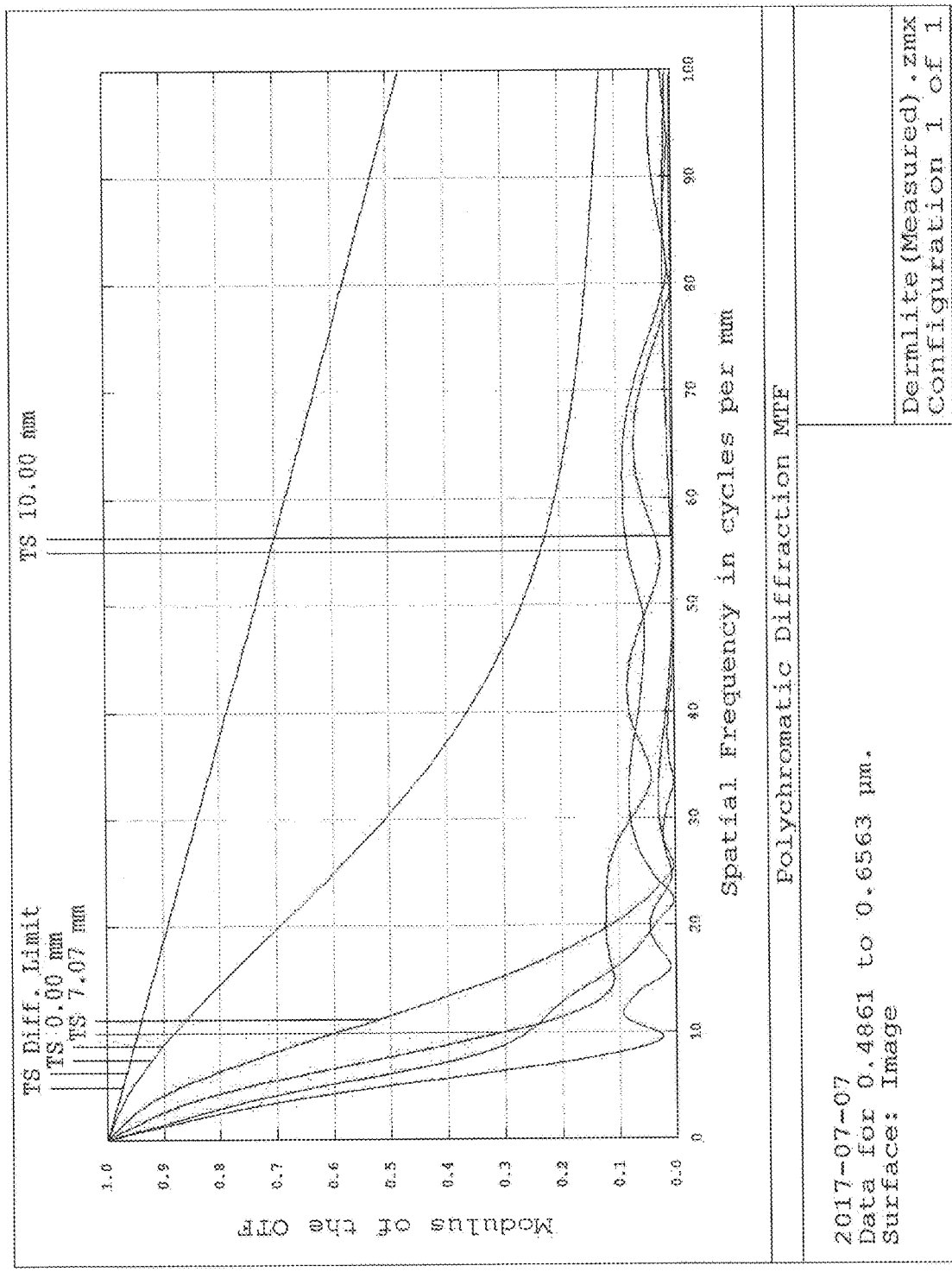
FIG. 11 is a graph illustrating an inspection result of optical resolution using a conventional dermatoscope device.
Figure 12:
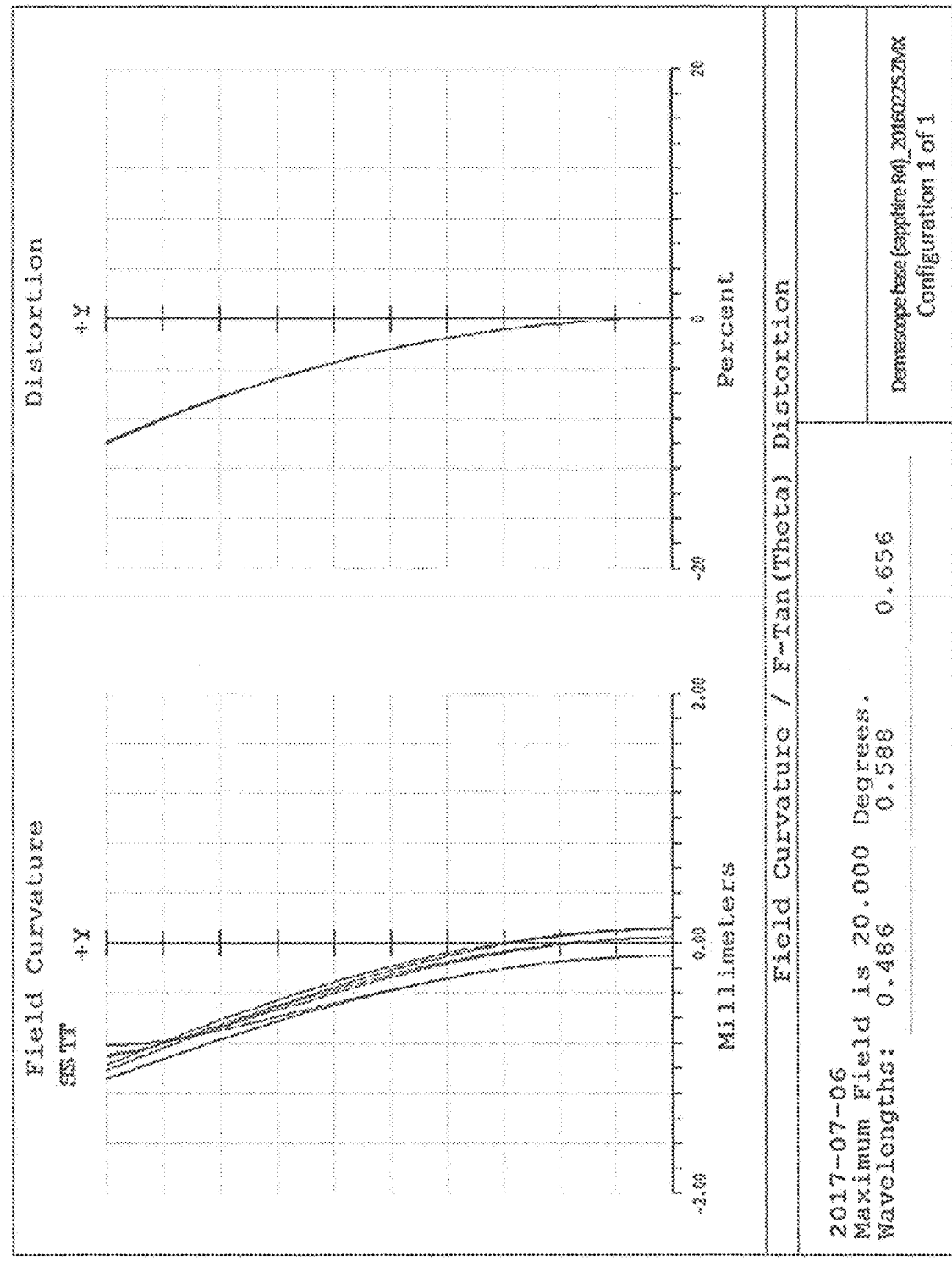
FIG. 12 is a graph illustrating an inspection result of optical distortion using the optical tube structure in the dermatoscope device, according to the inventive concept.

As illustrated in FIG. 11, the optical resolution measured using a conventional product of another company represents 0.15 Modulation Transfer Function (MTF) at the center and 0.05 MTF at the periphery, based on 75 LP (Line Pair) in the case of naked eyes Meanwhile, as illustrated in FIG. 10, the optical resolution measured using the dermatoscope device 1000 of the inventive concept represents 0.35 MTF at the center and 0.1 MTF at the periphery, based on 75 LP (Line Pair) in the case of naked eyes. Accordingly, the higher resolution may be represented in the inventive concept.

Figure 13:
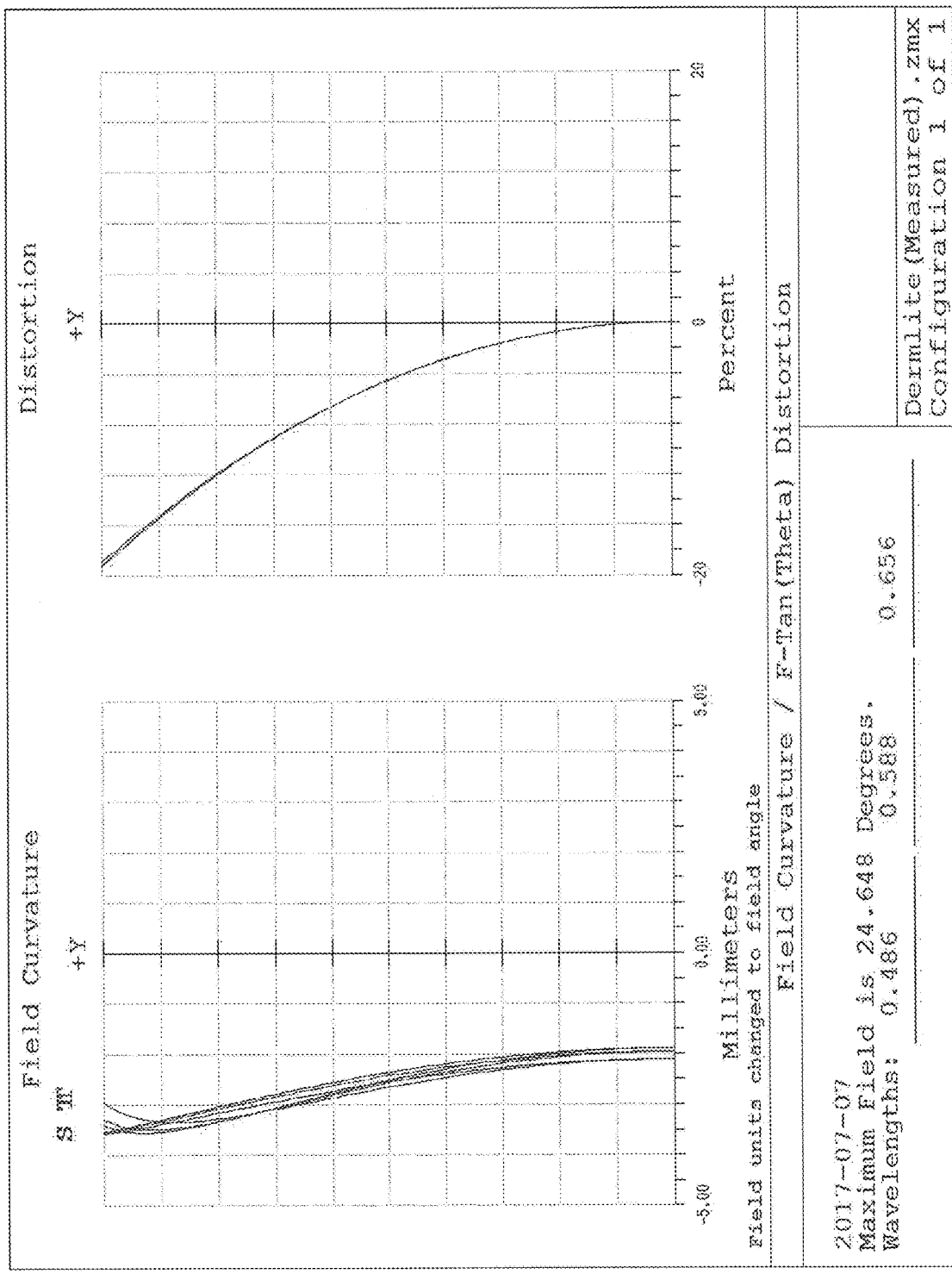
FIG. 13 is a graph illustrating an inspection result of optical distortion using the optical tube structure in the conventional dermatoscope device.

In addition, as illustrated in FIG. 13, the optical distortion measured by another product is about −10%, which represents the higher distortion degree. In contrast, the optical distortion factor measured by using the dermatoscope device 1000 of the inventive concept is about −4%. Accordingly, the observer rarely feels the distortion with naked eyes.

In addition, the diameters H of the first optical lens 1121, the second optical lens 1122A and the third optical lens 1122B constituting the chromatic aberration lens array 1122, and the second polarizing plate 1123 are 25 mm or more extending from the diameter of the conventional lens, which is in the range of 20 mm to 22 mm. Accordingly, the observation may be made throughout a wider area.

Figure 14:
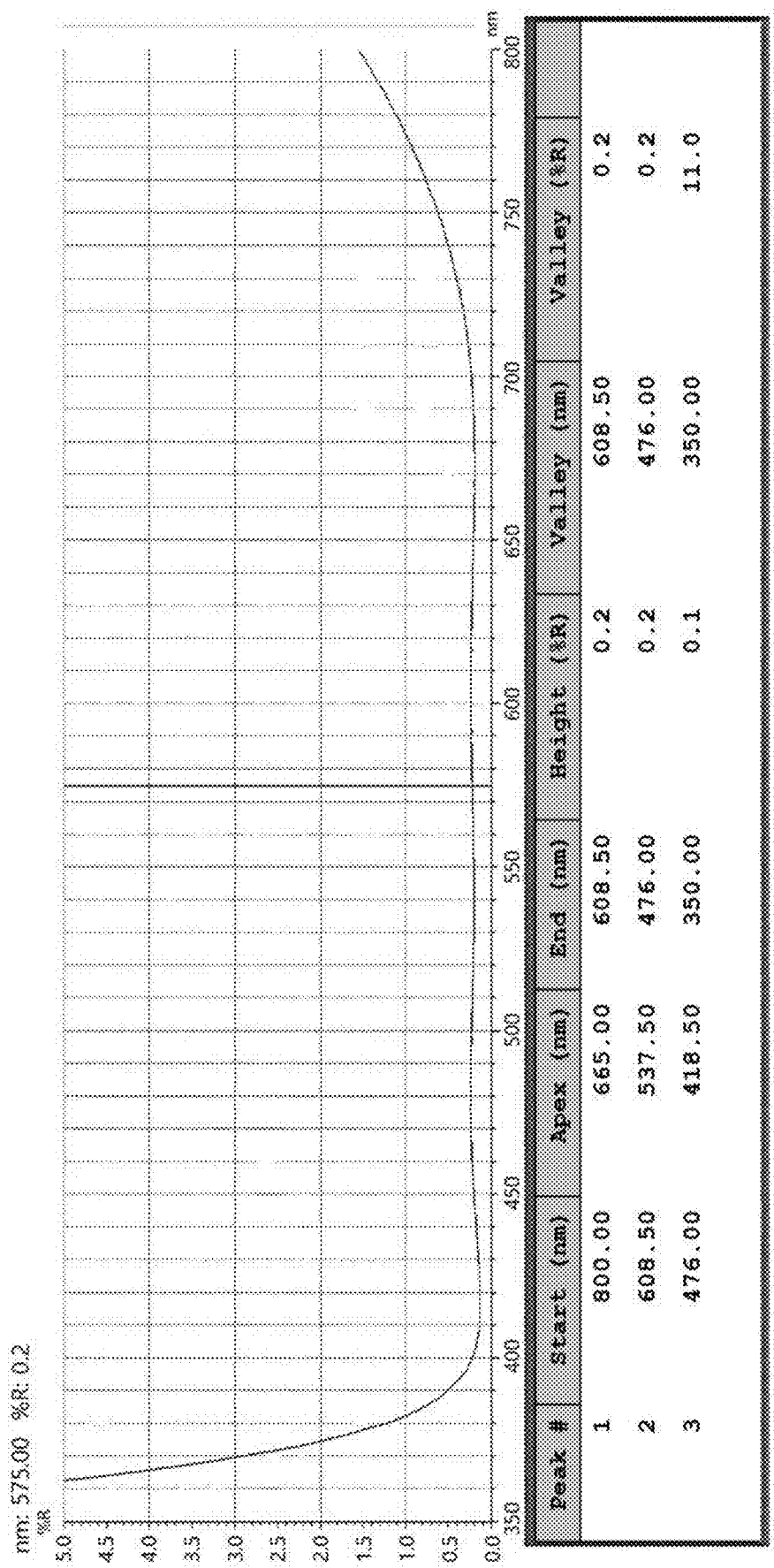
FIG. 14 is a graph illustrating the measurement result of a reflectance spectrum using the optical tube structure in the dermatoscope device, according to the inventive concept.

The measurement result of the light transmittance spectrum of the optical unit 1120, which is designed and provided as described above, using the spectrophotometer, may be examined to verify the above description. In other words, as illustrated in FIG. 14, differently from the conventional dermatoscope device, the transmittance of ultraviolet light and infrared light and the light reflectance are lowered and the transmittance of the visual light in the range of 380 nm to 780 nm is maximized to increase the optical definition for the observation target. Accordingly, observation may be stably and precisely made with the enlarged field of view. Simultaneously, the damage to the eyes of the observer and the fatigue degree of the observer resulting from the ultraviolet light and the infrared light may be significantly reduced.

Meanwhile, as illustrated in FIG. 4, the optical tube structure 1100 further include a first body part 1130, a second body part 1140, and a third body part 1150 to adjust the enlargement information by coupling the light emitting unit 1110 and the optical unit 1120 to the housing 1300 and by adjusting the focal length.

In this case, the first body part 1130 has a body structure in which the optical unit 1120 is mounted as illustrated in FIG. 4. When viewed from the whole structure, the first body part 1130 is provided at the center thereof with a first open space T1, which is used to mount the optical unit 1120 and open to ensure the field of view for observation after the optical unit 1120 is mounted, and is fixedly coupled to the housing 1300.

A second protective lens (not illustrated) may be provided in the opening, which is included in the first open space T1 of the first body part 1130 and positioned at the side of the observer P, such that the optical unit 1120 mounted inside the first body part 1130 may be protected from the outside.

In addition, the second body part 1140 has a body structure in which the light emitting unit 1110 is mounted as illustrated in FIG. 4. When viewed from the whole structure, the second body part 1140 is provided at the center thereof with a hollow space 1140T open to continuously ensure the field of view for observation ensured by the first body part 1130 in which the optical unit 1120 is mounted.

The hollow space 1140T provided at the center of the second body part 1140 forms a second open space T2 which is open to ensure the field of view for observation together with the light emitting unit 1110 mounted in the second body part 1140 and communicates with the first open space T1.

The second body part 1140 having the above structure is fixedly coupled to one side of the first body part 1130 or the housing 1300.

The third body part 1150 has a third open space T3 communicating with the second open space T2 to be open to continuously ensure the field of view for observation ensured through the first open space T1 of the first body part 1130 and the second open space T2 formed by the second body part 1140 and the light emitting unit 1110 mounted in the second body part 1140.

In this case, a first protective lens 1150L is mounted in an opening, which is provided in the third open space T3 of the third body part 1150 while being positioned at the observation target S, to protect, from the outside, the optical unit 1120 inside the first body part 1130 and the light emitting unit 1110 inside the second body part 1140, which are coupled to the third body part 1150. In addition, the first protective lens 1150L allows the observation through the emulsion oil.

The third body part 1150 having the above structure is coupled to the housing 1300 such that the third body part 1150 is movable back from and forth toward the observation target by external force applied to the housing 1300 from the outside.

To this end, the dermatoscope device 1000 of the inventive concept may further include the focal length adjustor 1600 serving as an additional adjusting unit coupled to the housing 1300 to be linked to the third body part 1150 to move the third body part 1150 back from and forth toward the observation target S.

In this case, the focal length adjustor 1600 serves as a component linked to the third body part 1150. When the focal length adjustor 1600 provided in the form of a rotator is rotated, the third body part 1150 linked to the focal length adjustor 1600 moves back from and forth toward the observation target S, thereby adjusting the enlargement degree of the observation target S, which is to be inspected by the observer P through the optical unit 1120, in zoom in or zoom out.

The inventive concept has the following effects.

First, the first polarizing part and the second polarizing part disposed in front of the first LED part and the second LED part are set to have polarizing axes be perpendicular to each other. As the multiple LED parts simultaneously emit light while distinguishing between the first LED parts and the second LED parts based on the operation of the polarization controlling input module, parallel polarizing and cross polarizing are selectively provided.

Second, the first LED parts and the second LED parts are alternately arranged at equal spacing on the light emitting base to provide the parallel polarizing and cross polarizing, thereby minimizing the deviation in the irradiation range of light and the quantity of light irradiated as the polarizing function is changed.

Third, as the quantity of light irradiated through the first LED part or the second LE part is variously controlled based on the operation of the brightness controlling input module, the light brightness is adjusted to be optimized to the skin color or the lesion on the skin of the patient.

Fourth, the optical resolution is more enhanced and the distortion degree is more reduced due to the first optical lens included in the optical unit, the chromatic aberration lens array (the second optical lens and the third optical lens), the spacing between the second polarizing plates, the arrangement form of the second polarizing plate, and the level of the radius of curvature for each lens.

While the inventive concept has been described with reference to embodiments, it will be apparent to those skilled in the art that various changes and modifications may be made without departing from the spirit and scope of the inventive concept. Therefore, it should be understood that the above embodiments are not limiting, but illustrative.

What is claimed is:

1. A dermatoscope device comprising:
an optical tube structure including an optical unit, which is provided to allow an observer to enlarge and inspect an observation target, and a light emitting unit which irradiates light to the observation target to be enlarged and inspected through the optical unit;
a control module configured to control a form of irradiating the light through the optical unit; and
a housing having the optical tube structure and the control module embedded therein,
wherein the light emitting unit includes:
a light emitting base including a plurality of first light emitting device (LED) parts simultaneously emitting light in response to a first light emitting signal received from the control module and a plurality of second LED parts simultaneously emitting light in response to a second light emitting signal received from the control module; and
a first polarizing plate including a plurality of first polarizing parts, which are positioned at a front portion in a direction that the light of the first LED parts is irradiated and have polarizing axes set to a first direction, and a plurality of second polarizing parts which are positioned at a front portion in a direction that the light of the second LED parts is irradiated and have polarizing axes set to a second direction perpendicular to the first direction, wherein the light emitting base including the plurality of first LED parts and the plurality of second LED parts has a disk-shape, wherein the light emitting base and the first polarizing plate are combined to configure a disk-type module having a hollow, wherein, in the disk-type module, the first polarizing plate is positioned so that each of the plurality of first polarizing parts and the plurality of second polarizing parts corresponds to each of the plurality of first LED parts and the plurality of second LED parts of the light emitting base, wherein the optical unit includes a second polarizing plate having polarizing axes set parallel with the first direction, and wherein the optical tube structure is configured to provide parallel polarizing by passing LED light though the first polarizing plate of the light emitting unit, and provide cross polarizing by passing LED light though the second polarizing plate of the optical unit.

2. The dermatoscope device of claim 1, wherein the first LED parts and the second LED parts are provided while alternately arranged at equal spacing in a circumferential direction along a specific virtual circumferential line on the light emitting base, and wherein the first polarizing parts and the second polarizing parts are provided corresponding to an alternate arrangement form of the first LED parts and the second LED parts provided on the light emitting base.

3. The dermatoscope device of claim 1, further comprising:

a polarization controlling input module configured to generate a first polarizing signal or a second polarizing signal and to transmit the first polarizing signal or the second polarizing signal to the control module, wherein the control module generates the first light emitting signal allowing the first LED parts to emit the light, when a signal received through the polarization controlling input module is the first polarizing signal, and wherein the control module generates the second light emitting signal allowing the second LED parts to emit the light, when the signal received through the polarization controlling input module is the second polarizing signal.

4. The dermatoscope device of claim 1, further comprising:

a brightness controlling input module configured to generate brightness control signals classified in at least three stages and to transmit the brightness control signals to the control module, wherein the control module controls brightness of the first LED parts or the second LED parts depending on a brightness stage indicated by a brightness control signal received through the brightness controlling input module.

5. The dermatoscope device of claim 1, further comprising:

a battery mounted inside the housing and configured to store and supply power required to operate the light emitting unit and the control module; and a charging port configured to supply power to the battery from an outside.

6. A dermatoscope device comprising:

an optical tube structure including an optical unit, which is provided to allow an observer to enlarge and inspect an observation target, and a light emitting unit which irradiates light to the observation target to be enlarged and inspected through the optical unit;

a control module configured to control a form of irradiating the light through the optical unit; and a housing having the optical tube structure and the control module embedded therein, wherein the light emitting unit includes:

a light emitting base including a plurality of first light emitting device (LED) parts simultaneously emitting light in response to a first light emitting signal received from the control module and a plurality of second LED parts simultaneously emitting light in response to a second light emitting signal received from the control module; and a first polarizing plate including a plurality of first polarizing parts, which are positioned at a front portion in a direction that the light of the first LED parts is irradiated and have polarizing axes set to a first direction, and a plurality of second polarizing parts which are positioned at a front portion in a direction that the light of the second LED parts is irradiated and have polarizing axes set to a second direction perpendicular to the first direction, wherein the optical unit includes:

a first optical lens positioned at a side of the observer and provided in a form of a sectional-surface convex lens which has a convex surface at a side of an observation target;

a chromatic aberration lens array positioned in front of the first optical lens at the side of the observation target and having convex opposite surfaces; and a second polarizing plate positioned in front of the chromatic aberration lens array at the side of the observation target and having a polarizing axis set in parallel to the first direction, and wherein a radius of curvature of a convex surface of the first optical lens at the side of the observation target is greater than a radius of curvature of a convex surface of the chromatic aberration lens array at a side of the observer and is less than a radius of curvature of a convex surface of the chromatic aberration lens array at the side of the observation target.

7. The dermatoscope device of claim 6, wherein the chromatic aberration lens array includes:

a second optical lens positioned in front of the first optical lens at the side of the observation target and having a form of a double-sided convex lens having opposite sides which are convex; and a third optical lens having a form of a negative meniscus lens having a surface which is positioned at the side of the observation target and is concave corresponding to a convex shape of the surface of the second optical lens at the side of the observer while making contact with the surface of the second optical lens at the side of the observer, and a surface which is positioned at the side of the observer is convex, and wherein the radius of curvature of the convex surface, which corresponds to the convex surface of the chromatic aberration lens array at the side of the observer, of the second optical lens at the side of the observer is greater than a radius of curvature of the convex surface of the second optical lens at the side of the observation target and is less than the radius of curvature of the convex surface, which corresponds to the convex surface of the chromatic aberration lens array at the side of the observation target, of the third optical lens at the side of the observation target.

8. The dermato scope device of claim 6, wherein the optical unit further includes:
   a first spacer spacing the first optical lens apart from the chromatic aberration lens array by a first distance; and
   a second spacer spacing the chromatic aberration lens array apart from the second polarizing plate by a second distance, and
   wherein the first distance, which is formed as central axes of the first optical lens and the chromatic aberration lens array are spaced apart from each other by the first spacer, is shorter than the second distance which is formed as the central axes of the chromatic aberration lens array and the second polarizing plate are spaced apart from each other by the second spacer.

9. The dermatoscope device of claim 6, wherein the optical tube structure includes:
   a first body part having the optical unit mounted therein, having a first open space, which is open to ensure the field of view for observation, and fixedly coupled to the housing;
   a second body part having the light emitting unit mounted therein, having a second open space, which is open to ensure the field of view for observation together with the mounted light emitting unit and communicates with the first open space, and fixedly coupled to the first body part or the housing; and
   a third body part having a third open space, which is open to ensure the field of the view for observation and communicates with the second open space, and a first protective lens provided in an opening of the third open space at the side of the observation target, and coupled to the housing movably back from and forth toward with respect to the observation target.

10. The dermatoscope device of claim 9, further comprising:
   a focal length adjustor coupled to the housing to be linked to the third body part to move the third body part back from and forth toward the observation target such that an enlargement degree of the observation target, which is to be inspected by the observer through the optical unit, is adjusted in zoom in or zoom out.

* * * * *